(12) United States Patent
Cook

(10) Patent No.: US 6,384,027 B1
(45) Date of Patent: May 7, 2002

(54) PHTHALOCYANINE ANALOGS

(75) Inventor: Michael J Cook, Norwich (GB)

(73) Assignee: QinetiQ Limited, Farnborough (GB)

( * ) Notice: Subject to any disclaimer, the term of this patent is extended or adjusted under 35 U.S.C. 154(b) by 0 days.

(21) Appl. No.: 09/529,673

(22) PCT Filed: Oct. 26, 1998

(86) PCT No.: PCT/GB98/03185

§ 371 Date: Apr. 18, 2000

§ 102(e) Date: Apr. 18, 2000

(87) PCT Pub. No.: WO99/23096

PCT Pub. Date: May 14, 1999

(30) Foreign Application Priority Data

Oct. 30, 1997 (GB) ............................................. 9722883

(51) Int. Cl.[7] ...................... A61K 31/706; A61K 31/33; C07D 487/22; C07F 19/00
(52) U.S. Cl. ...................... 514/189; 514/183; 514/184; 252/299.61; 252/301.26; 252/587; 534/15; 540/121; 540/122; 540/124; 540/139; 540/140
(58) Field of Search ................................ 514/184, 183, 514/189; 540/122, 139, 140, 121, 124; 534/15

(56) References Cited

U.S. PATENT DOCUMENTS

| 4,252,875 A | 2/1981 | Venkatasetty ............... 429/196 |
| 5,484,778 A | 1/1996 | Kenney et al. ............... 514/63 |
| 5,580,696 A | 12/1996 | Yashiro ................. 430/270.17 |
| 5,618,929 A | 4/1997 | Harrison et al. ............ 540/139 |

FOREIGN PATENT DOCUMENTS

| DE | 3518804 A1 | 11/1985 |
| EP | 344891 A2 | 12/1989 |
| GB | 2 159 516 | 12/1985 |
| JP | 02033156 A2 | 2/1990 |
| JP | 09013024 | 11/1997 |
| WO | 96/19480 | 6/1996 |

OTHER PUBLICATIONS

Cook et al., J. Mater. Chem., 1997, 7(12), pp. 2327–9.*
Kazufumi et al., 1990; 581342 CAPLUS Only Abst is provided (p. 490 ).*
M.J. Cook et al.: "Pyridino '3, 4! tribenzoporphyrazines: edge–to–face versus face–to–face assemblies among phthalocyanine analogues" Journal of Materials Chemistry, vol. 7, No. 12, 1997, pp. 2327–2329, XP002092152 Cambridge, UK, see compounds 1a, 1b, 1c.

Chemical Abstracts, abstr No. 62:14860a, 1965, vol. (23)2, pp 151–155 see compound RN 14245–24–0.
Chemical Abstracts, abstr. No. 76:140453 1970 No. 2 pp 327–329 see compound RN36619–89–3.

* cited by examiner

Primary Examiner—John M. Ford
(74) Attorney, Agent, or Firm—Nixon & Vanderhye

(57) ABSTRACT

Disclosed are compounds of formula V

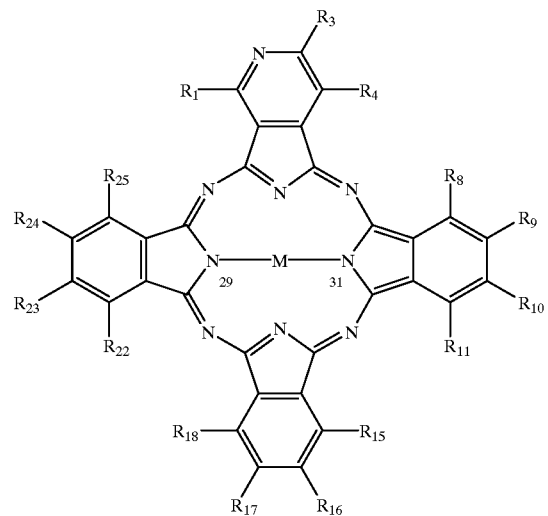

Formula V wherein M is selected from: a metal atom; a metal compound; 2H whereby one H is bonded to each of the two nitrogen atoms depicted as being bonded to M (positions 29 and 31 shown) $R_3$ is H or methyl; $R_1$ and $R_4$ are independently selected from: H, $C_1$ to $C_4$ alkyl, $C_2$ to $C_4$ alkenyl, methoxy, butoxy, propoxy, $NH_2$, NH—($C_1$ to $C_4$ alkyl), N—($C_1$ to $C_4$ alkyl)$_2$, S—($C_1$ to $C_4$ alkyl); $R_8$ to $R_{25}$ are the same or different and are independently selected from: $C_1$ to $C_{32}$ alkyl; $C_2$ to $C_{32}$ alkenyl; X—O—Y; X—phenyl, $X^2COOX^1$, $X^2CONR^1R^{11}$, H; halide; wherein: X and $X^2$ are independently selected from: a chemical bond, —$(CH_2)_n$— wherein n is an integer from 1 to 32, —$(CH_2)_a$—CH=CH$(CH_2)_b$ where a and b are independently selected from integers 0–32 and a+b totals 32; $X^1$ and Y are independently selected from: $C_1$ to $C_{32}$ alkyl, $C_2$ to $C_{32}$ alkenyl, and H; $R^1$ and $R^{11}$ are independently selected from: H; $C_1$ to $C_{32}$ alkyl, $C_2$ to $C_{32}$ alkenyl, —$(CH_2)_n$—; with the proviso that at least one of $R_8$ to $R_{25}$ is selected from: $C_1$ to $C_{32}$ alkyl, $C_2$ to $C_{32}$ alkenyl, X—O—Y, X—phenyl, $X^2COOX^1$, $X^2CONR^1 R^{11}$.

11 Claims, 7 Drawing Sheets

= Pc

Formula I

Formula II

Formula III

Formula IV

Formula V

Formula VI (zinc octahexylPc)
(6Zn)

Spin coated films

Metal free macrocycle

Nickel macrocycle

Zn macrocycle

Zn + HCl vapour

80 R = $C_8H_{17}$, M = 2H (1a)
81 R = $C_8H_{17}$, M = Ni (1b)
82 R = $C_8H_{17}$, M = Cu
83 R = $C_8H_{17}$, M = Zn (1c)
84 R = $C_8H_{17}$, M = Co
85 R = $C_6H_{13}$, M = 2H
86 R = $C_6H_{13}$, M = Zn
87 R = $C_4H_9$, M = 2H

Scheme 1

PHTHALOCYANINE ANALOGS

The present invention relates to phthalocyanine analogs, in particularly to azaphthalocyanines (pyridinoporphyrazines). It further relates to compositions containing these compounds, and methods of use of such compounds and compositions.

Phthalocyanine is shown in FIG. 1 (*a*). The nomenclature for the numbering of the Benzo portion is also included in the above depiction. Generally substituents in the R2, 3, 9, 10, 16, 17, 23, 24 positions are referred to as peripheral groups and substituents in the R1, 4, 8, 11, 15, 18, 22, 25 positions are referred to as non-peripheral groups.

Often, phthalocyanine is abbreviated to Pc.

Pcs in condensed phases possess interesting optical absorption signatures. semiconductivity and optoelectronic properties which are often sensitive to molecular packing. Normally, the planar molecules are prone to form co-facial or near co-facial assemblies. These "Face-to-Face" structures include the simple aggregates found in solution,[2] the longer columnar stacks in the liquid crystal phases of mesogenic derivatives,[3] and the classic "herring bone" columnar packing in the most common polymorphs of the unsubstituted compounds.[4] Polymeric columnar structures include the "shish-kebab" polymers formed when the central metal atoms of neighbouring Pc units are covalently or coordinatively linked via bridging atoms or molecules.[5]

The unusual properties that Pcs and Pc analogs exhibit means they have many applications.

UK Patent GB 2,229,190 B relates to certain novel substituted phthalocyanines, methods for their preparation and to certain uses thereof. For example the compounds described in GB 2,229,190 B are suitable for use in optical recording media. Kuder in J. of Imaging Science, vol. 32, (1988), pp51–56 discusses how phthalocyanine dyes may be used in laser addressed optical recording media; in particular it sets out how active layers may be deposited.

UK Patent Application 9317881.2 describes substituted metallophthalocyanines and phthalocyanines as PDT agents.

Patent application WO 93/09124 describes the use of water soluble salt or acid forms of transition metal phthalocyanines for use in photodynamic therapy. In this patent application, phthalocyanines containing second or third row transition metals with a d6 low-spin electronic configuration are disclosed. The compounds exemplified in patent application WO 93/09124 contain Ru.

Phthalocyanine derivatives have also been used in Langmuir Blodgett films as described in UK Patent 2,229,190 B.

The redox behaviour of phthalocyanines is also of interest. Some uses which exploit the redox properties of phthalocyanines include electrocatalysis, photocatalysis, photovoltaics, electric conduction, photoconductivity and electrochromism. These uses (amongst others) of phthalocyanines are discussed by A. B. P. Lever in Chemtech, 17, pp506–510, 1987.

Certain pyridinoporphrazines (azaphthalocyanines, or AzaPcs) have been prepared and reported in the literature. These include tetrapyridino derivatives and bipyridino derivatives having Cr, Co, Cu, Fe and Ni centres. Thus Linstead[7] first demonstrated the replacement of all four benzene rings of the Pc nucleus by pyridine in his classic investigations in the 1930s, obtaining a mixture of insoluble isomeric dyes from 3,4-dicyanopyridine. Subsequently, Shibamiya and coworkers prepared unsubstituted macrocycles containing combinations of both benzenoid and pyridinoid rings.[8] The absorption spectra of these compounds were described, although not with reference to any particular applications.

It can thus be seen that the provision of novel Pc derivatives (or uses for such derivatives) particularly those with novel absorption signatures, would provide a contribution to the art.

DISCLOSURE OF THE INVENTION

The present inventors have now produced and characterised novel organic solvent-soluble AzaPcs in which a pyridinoid ring is incorporated in or around the Pc nucleus. Such compounds provide, inter alia, for the generation of "Edge-to-Face" assemblies via metal-nitrogen coordination involving the pyridyl nitrogen atom of one molecule and the metal ion of a second molecule.

Although Edge-to-Face assembles have been constructed earlier using porphyrin derivatives,[6] they have not as yet been realised within the Pc series. Such compounds have unexpected and industrially applicable properties in a variety of technical fields as is described in further detail hereinafter.

Thus according to one aspect of the invention there is disclosed an AzaPc of Formula I (FIG. 1(*b*)):

wherein:

M is selected from:
a metal atom; a metal compound; 2H whereby one H is bonded to each of the two nitrogen atoms depicted as being bonded to M (positions 29 and 31 shown)

and wherein:
one or more of the Q groups is selected from: formula II or formula III, with the remaining Q groups each being formula IV:

wherein:

$R_{33}$ and $R_{34}$ are independently selected from: H or methyl $R_{35}$ is selected from: H; $C_1$ to $C_4$ alkyl; $C_2$ to $C_4$ alkenyl; methoxy; butoxy; propoxy; $NH_2$; NH—($C_1$ to $C_4$ alkyl); N—($C_1$ to $C_4$ alkyl)$_2$, S—($C_1$ to $C_4$ alkyl).

each $R_n$ and $R_p$ group is independently selected from: $C_1$ to $C_{32}$ alkyl; $C_2$ to $C_{32}$ alkenyl; X—O—Y; X—phenyl $X^2COOX^1$; $X^2CONR^1R^{11}$; H; halide wherein:

X and $X^2$ are independently selected from: a chemical bond; —(CH$_2$)$_n$— wherein n is an integer from 1 to 32; —(CH$_2$)$_a$—CH=CH(CH$_2$)$_b$ where a and b are independently selected from integers 0–32 and a+b totals 32.

$X^1$ and Y are independently selected from: $C_1$ to $C_{32}$ alkyl; $C_2$ to $C_{32}$ alkenyl; H $R^1$ and $R^{11}$ are independently selected from: H; $C_1$ to $C_{32}$ alkyl; $C_2$ to $C_{32}$ alkenyl; —(CH$_2$)$_n$— with the proviso that where more than one Q is Formula II with the remaining Q group being Formula IV, at least one of the $R_{33}$, $R_{34}$, $R_{35}$, $R_n$, or $R_p$ groups is not H.

In a further, preferred aspect of the invention, there is disclosed an AzaPc having formula V (FIG. 1(*f*)).

Wherein:

M is selected from:
a metal atom; a metal compound; 2H whereby one H is bonded to each of the two nitrogen atoms depicted as being bonded to M (positions 29 and 31 shown)

$R_3$ is H or methyl $R_1$ and $R_4$ are independently selected from: H; $C_1$ to $C_4$ alkyl; $C_2$ to $C_4$ alkenyl; methoxy; butoxy; propoxy; $NH_2$; NH—($C_1$ to $C_4$ alkyl); N—($C_1$ to $C_4$ alkyl)$_2$, S—($C_1$ to $C_4$ alkyl).

$R_8$ to $R_{25}$ are the same or different and are independently selected from:

$C_1$ to $C_{32}$ alkyl; $C_2$ to $C_{32}$ alkenyl; X—O—Y; X—phenyl $X^2COOX^1$; $X^2CONR^1R^{11}$; H; halide wherein:

X and $X^2$ are independently selected from: a chemical bond: —$(CH_2)_n$— wherein n is an integer from 1 to 32; —$(CH_2)_a$—CH=CH$(CH_2)_b$ where a and b are independently selected from integers 0–32 and a+b totals 32.

$X^1$ and Y are independently selected from: $C_1$ to $C_{32}$ alkyl; $C_2$ to $C_{32}$ alkenyl; H $R^1$ and $R^{11}$ are independently selected from: H; $C_1$ to $C_{32}$ alkyl; $C_2$ to $C_{32}$ alkenyl; —$(CH_2)_n$—

Most preferably the compound has formula VI (as shown in FIG. 1(g), wherein M=2H, Ni, Zn, Co, Cu, Pd, Ru or Al.

Referring to formula I, formula VI has one Q group of formula II with the remaining Q groups each being formula IV. $R_{33}$, $R_{34}$ and $R_{35}$ are H; $R_n$ are $C_8$ alkyl and $R_p$ is H.

Preferred Compounds

Preferred compounds of the present invention are those wherein any one or more of the following apply:

All non-peripheral R groups (e.g. $R_n$ in formula III and IV) are H.

All R groups other than those attached to pyridyl nuclei are alkyl containing up to 32 (preferably up to 20, more preferably between 4–14 or between 8–12) C atoms where 1 or more adjacent $CH_2$ groups may be replaced by O or a double bond, and the remaining R groups are all H.

All peripheral R groups other than those attached to pyridyl nuclei are alkyl containing up to 32 (preferably up to 20, more preferably between 4–14 or between 8–12) C atoms, and the remaining R groups are all H.

The R groups attached to the or each pyridyl nucleus on the C atoms adjacent the N (i.e. $R_{33},R_{34},R_1,R_3$ as appropriate) are H, thereby minimising steric hindrance in those embodiments of the invention which form "edge-to-face" dimers or higher oligomers.

The R group attached to the or each pyridyl nucleus which is in the meta-position with respect to the N (i.e. $R_{35}$ or $R_4$ as appropriate) is an electron donating group thereby increasing the basicity of the N such as to enhance its properties as a ligand.

Examples of this type of group include O-alkyl. $NH_2$, NH-alkyl, N(alkyl)$_2$, alkyl, S-alkyl.

In all cases the alkyl groups may be straight or branched chain. Straight chain are preferred.

The compounds of the invention may be metal free or contain a metal bound to a ligand (such compounds may have utility, inter alia, in the manufacture of metal containing derivatives, for instance as intermediates) or may contain a metal atom, preferably a diamagnetic metal atom.

The metal atom may be present for example as the metal with an oxidation state of +2 or it may be present with other ligands (or anions) attached to it. These ligands (or anions) may serve the purpose of altering the hydrophobicity of the molecule as a whole. Examples of suitable anions include chloride, bromide or oxide. Examples of suitable metals include Ru, Ni, Pb, V, Pd. Co, Nb, Al, Sn, Zn, Cu, Mg, Ca, In, Ga, Fe, Eu, Lu and Ge. Preferably when M is a metal or metal compound then the metal is, or the metal compound contains Cu, Zn, Ru, Pb, V, Co, Eu, Lu, Al. Examples of suitable metal compounds include VO and TiO. Those which may preferentially form "edge-to-face" dimers or higher oligomers under appropriate conditions include Zn, Cu, Co, Ru, and Ni.

Applications

Methods of use of the compounds described above form further aspects of the present invention. Some particular applications are exemplified below:

PDT

In this application it is preferred that M in the compounds of the present invention is diamagnetic e.g. a second or third row transition metal with a $d^6$ low-spin electronic configuration, preferably Zn. Ru-containing compounds may also be advantageous.

A number of Pc derivatives have previously been proposed as potential photodynamic therapeutic (PDT) agents. The combination of a sensitizer and electromagnetic radiation for the treatment of cancer is commonly known as photodynamic therapy. In the photodynamic therapy of cancer, dye compounds are administered to a tumour-bearing subject. These dye substances may be taken up, to a certain extent, by the tumour. Upon selective irradiation with an appropriate light source the tumour tissue is destroyed via the dye mediated photo-generation of species such as singlet oxygen or other cytotoxic species such as free radicals, for example hydroxy or superoxide. Most biological studies on Pc compounds related to PDT have been conducted with water soluble sulfonated metallophthalocyanines as described by I. Rosenthal, Photochem. Photobiol. 53(6), 859–870, 1991. Methods for synthesizing these compounds often results in mixtures of compounds containing a variety of isomers and/or different degrees of sulfonation.

Ideally compounds for use as photosensitizers in PDT have some or all of the following characteristics: solubility; high quantum yield of reactive species; low toxicity; high absorption coefficients, preferably in the red or near infra red of the spectrum; selective accumulation in the tumour.

The reason why absorption in the red-region of the EM spectrum is desirable is that red light shows greater penetration than light of shorter wavelengths. Such sensitisers can be irradiated e.g. with laser light, or from other non-laser sources e.g. tungsten halogen light.

The compounds of the present invention are particularly advantageous in this regard because of their spectral properties, their ability to form high concentrations of dimers which fluoresce, and their solubility. Preferred compounds have Zn ,Ru or Al as their metal centre, since these have previously been shown (in other PCs) to be effective generators of singlet oxygen.

One aspect of the present invention provides a pharmaceutical composition comprising a compound of the invention (e.g Formula VI wherein M is Zn or Ru) in a mixture or in association with a pharmaceutically acceptable carrier or diluent.

Also embraced is use of such a compound in the preparation of a medicament, preferably a medicament for treatment against cancer, most preferably for the treatment of a mammal having a tumour susceptible to photodynamic treatment.

In a further aspect, the invention also includes a method of treatment of a mammal having a tumour susceptible to photodynamic treatment, wherein the mammal is administered an effective dose of a compound of formula I or a pharmaceutically acceptable salt form thereof and the tumour is subjected to suitable electromagnetic radiation.

The compounds described by the present invention may be induced to act as a photosensitizers by incident electromagnetic radiation of a suitable wavelength. Preferably, the electromagnetic radiation is somewhere in the range ultra-violet to infra-red, even more preferably it is in the range visible to red to near infra-red.

The pharmaceutical compositions may be formulated according to well-known principles and may desirably be in the form of unit dosages determined in accordance with conventional pharmacological methods. The unit dosage forms may provide daily dosage of active compound in a single dose or in a number of smaller doses. Dosage ranges may be established using conventional pharmacological methods and are expected to lie in the range 1 to 60 mg/kg of body weight. Other active compounds may be used in the compositions or administered separately, or supplemental therapy may be included in a course of treatment for a patient. The pharmaceutical compositions may desirably be in the form of solutions of suspensions for injection or in forms for topical application including application in for example the oral cavity. Application in other cavities is also possible. Suitable carriers and diluents are well known in the art and the compositions may include excipients and other components to provide easier or more effective administration.

Following administration to the patient, photodynamic therapy may be carried out in a conventional manner, using light sources and delivery systems that are known in the art, for example, see Phys. Med. biol. (1986), 31, 4, 327–360.

Enhanced positioning of the compounds of formula I in relation to treating tumours may be achieved. For example, the compounds of the present invention may be combined with other chemical moieties.

Thus a further aspect embraces compositions comprising such compounds plus a targeting molecule (e.g. an antibody) which may be part of a binding pair, the other member of the pair being located or concentrated in the target site (e.g. an antigen associated with a tumour). A particular compound could be combined, for example, by chemical attachment, with an antibody tailored to attach itself to the tumour site. Antibodies as prepared from cultured samples of the tumour. Examples include P.L.A.P. (Placental Alkaline Phosphatase), H.M.F.G. (Human Milk Fat Globulin), C.E.A. (Carcino Embryonic Antibody), H.C.G. (Human Chorionic Gonadotrophin).

Other targeting molecules may include lectins, protein A, nucleic acids (which bind complementary nucleic acids) etc.

Further possible uses of Pcs (as photosensitizers) include use as anti-virals in blood-banks or insecticides.

LCDs

It is well known that some phthalocyanine compounds exhibit liquid crystalline behaviour.

The majority of known liquid crystalline compounds have a generally rod-shaped molecular structure and are often characterised by nematic and/or smectic mesophases. There are, however, a number of known compounds which are characterised by a generally disc-like molecular structure. These compounds are termed discotic compounds, which can be characterised by discotic nematic or columnar mesophase(s).

Discotic compounds can be based on a number of "cores", e.g. benzene, truxene, metallophthalocyanine, phthalocyanines and triphenylene.

Certain compounds of the present invention e.g. Ni, Cu, Co and 2H containing compounds, have been demonstrated to exhibit columnar mesophases.

Guillon et al Mol. Cryst. Liq. Cryst.; 1985, vol. 130, pp223–229, discuss columnar mesophases from metallated and metal free derivatives of phthalocyanine in which the phthalocyanine is substituted on the benzene rings with various groups all of which are attached to the phthalocyanine core via a $CH_2$ unit.

Piechocki and Simon, New Journal of Chemistry, vol. 9, no 3, 1985, pp159–166, report the synthesis of octa-substituted phthalocyanine derivatives forming discotic mesophases. The side chains are linked to the phthalocyanine core via a $CH_2$ unit.

Most liquid crystal compounds are known as thermotropic liquid crystal compounds. Thermotropic liquid crystals exist in dependence of the temperature in certain temperature intervals. In some cases when different substances are mixed together with a solvent the mixture can exhibit different phases not only as the temperature is changed, but also as the concentration of the solute is changed. When the liquid crystal phase is dependent on the concentration of one component in another it is called a lyotropic liquid crystal. The easiest way to make a lyotropic liquid crystal mixture is to start with a molecule that possesses end groups with different properties. For example one end could show an affinity for water and the other end tends to exclude water. Molecules which possess both a hydrophilic group and a part which is a hydrophobic group can display characteristics of both classes, therefore they are called amphiphilic molecules.

Lyotropic liquid crystals have numerous potential applications including detergents, the recovery of oil from porous rocks and in the food industry, providing they are sufficiently non-toxic, for example as food emulsifiers. There may also be medical applications for lyotropic liquid crystal systems. For example, amphiphilic materials could help to make drugs more soluble in the blood.

For a review of phthalocyanine thermotropics, see Simon and Bassoul in Phthalocyanines, Properties and Applications, Ed., C. C. Leznoff and A. B. P. Lever, V. C. H. Publishers 1992, p227.

Liquid Crystal Devices

One aspect of the invention includes use of the compounds of Formula I, and use of mixtures including Formula I, in a liquid crystal device. Typically such devices include linear and non-linear electrical, optical and electro-optical devices, magneto-optical devices, and devices providing responses to stimuli such as temperature changes and total or partial pressure changes. The devices themselves form a further aspect of the present invention.

A typical example of the use of a compound of Formula I in a liquid crystal material and device embodying the present invention will now be described with reference to FIG. 4.

The liquid crystal device consists of two transparent plates, 1 and 2, in this case made from glass. These plates are coated on their internal face with transparent conducting electrodes 3 and 4. An alignment layer 5, 6 is introduced onto the internal faces of the cell so that a planar orientation of the molecules making up the liquid crystalline material will be approximately parallel or at a small angle to the glass plates 1 and 2. For some types of display the plane of the molecules is approximately perpendicular to that of the glass plates, and at each glass plate the alignment directions are orthogonal. The electrodes 3, 4 may be formed into row and column electrodes so that the intersections between each column and row form an x, y matrix of addressable elements or pixels. A spacer 7 e.g. of polymethyl methacrylate separates the glass plates 1 and 2 to a suitable distance e.g. 2 microns. Liquid crystal material 8 is introduced between glass plates 1, 2 by filling the space in between them. The spacer 7 is sealed with an adhesive 9 in a vacuum using an existing technique. Polarisers 10, 11 are arranged in front of and behind the cell. For some devices, only one or even no polarisers are required.

The device may operate in a transmissive or reflective mode. In the former, light passing through the device, e.g. from a tungsten bulb, is selectively transmitted or blocked to form the desired display. In the reflective mode a mirror (12) is placed behind the second polariser 11 to reflect ambient light back through the cell and two polarisers. By making the mirror partly reflecting the device may be operated both in a transmissive and reflective mode.

The alignment layers 5,6 have two functions one to align contacting liquid crystal molecules in a preferred direction and the other to give a tilt to these molecules—a so called surface tilt—of a few degrees typically around 4E or 5E. The alignment 5, 6 may be formed by placing a few drops of the polyimide onto the cell wall and spinning the wall until a uniform thickness is obtained. The polyimide is then cured by heating to a predetermined temperature for a predetermined time followed by unidirectional rubbing with a roller coated with a nylon cloth.

Laser Addressed Applications

Some phthalocyanines also absorb radiation in the far-red to near infra-red regions of the electromagnetic spectrum. Compounds which absorb strongly at wavelengths of laser light can in principle be exploited as guest dyes dissolved in liquid crystalline host materials in a laser addressed system.

Materials have been proposed for laser addressed applications in which laser beams are used to scan across the surface of the material or leave a written impression thereon. For various reasons, many of these materials have consisted of organic materials which are at least partially transparent in the visible region. The technique relies upon localised absorption of laser energy which causes localised heating and in turn alters the optical properties of the otherwise transparent material in the region of contact with the laser beam. Thus as the beam traverses the material, a written impression of its path is left behind. One of the most important of these applications is in laser addressed optical storage devices, and in laser addressed projection displays in which light is directed through a cell containing the material and is projected onto a screen. Such devices have been described by Khan Appl. Phys. Lett. Vol. 22, p111, 1973; and by Harold and Steele in Proceedings of Euro display 84, pages 29–31, September 1984, Paris, France, in which the material in the device was a smectic liquid crystal material. Devices which use a liquid crystal material as the optical storage medium are an important class of such devices. The use of semiconductor lasers, especially $Ga_xAl_{1-x}As$ lasers where x is from 0 to 1, and is preferably 1, has proven popular in the above applications because they can provide laser energy at a range of wavelengths in the near infra-red which cannot be seen and thus cannot interfere with the visual display, and yet can provide a useful source of well-defined, intense heat energy. Gallium arsenide lasers provide laser light at wavelengths of about 850 nm, and are useful for the above applications. With increasing Al content (x<1), the laser wavelength may be reduced down to about 750 nm.

One of the main problems associated with the use of the above materials is that it has proved difficult to provide materials which are transparent in the visible region and yet are strong absorbers in either the UV or IR region, preferably in the near-IR region. The use of dyes within these materials can provide strong absorption at certain wavelengths, but few dyes are transparent in the visible region and many are insoluble in the type of materials used for laser addressed applications. EP-A-0155780 discloses a group of metal and metal-free phthalocyanines which have been used as infra-red absorbing dyes for a number of applications. These phthalocyanines contain from 5 to 16 peripheral organic substituent groups that are linked to the phthalocyanine through sulphur, selenium, tellurium, nitrogen or oxygen atoms. However, very few of the groups disclosed absorb infra-red radiation strongly at or near the wavelength of a gallium arsenide laser (850 nm). This problem also applies to a further group of infra-red absorbing phthalocyanines disclosed in EP-A-0134518. This further group consists of naphthalocyanines which are peripherally substituted with alkyl groups and centrally substituted with a metal atom or a chloride, bromide or oxide thereof. Materials Science II/1-2, 1976 pp 39–45 discloses the synthesis of octamethoxyphthalocyanines but these are insoluble in organic solvents and as such are unsuitable for acting as dyes in liquid crystalline solvents for laser addressed systems. Various of the compounds of the present invention are particularly suitable for this application owing to their high solubility and the retention of high absorbance at appropriate wavelengths even at high concentrations. The absorption maxima may be controlled by altering the central atom, or by use of additives (e.g. metal salts) or other agents to (e.g. pyridine to decomplex ZnAzaPc).

Optical Recording Media

For corresponding reasons to those discussed above, the compounds of the present invention will be suitable for use in optical recording media. Typically the phthalocyanine will absorb in the near-infrared. In order to make an optical recording media using a near-infrared absorber, the near-infrared absorber may be coated or vacuum-deposited onto a transparent substrate. European patent application EP 0 337 209 A2 describes the processes by which the above optical-recording media may be made. Further the materials described in EP 0 337 209 A2 are useful in near-infrared absorption filters and liquid crystal display devices, as are the compounds described by the current invention. As described in EP 0 337 209 A2, display materials can be made by mixing a near-infrared absorber of formula I with liquid crystal materials such as nematic liquid crystals, smectic liquid crystals and cholestric liquid crystals. The compounds of the current invention may be incorporated into liquid crystal panels wherein the near-infrared absorber is incorporated with the liquid crystal and laser beam is used to write an image. Mixtures of phthalocyanines of the current invention may be mixed with liquid crystal materials in order to be used in guest-host systems. GB 2,229,190 B describes the use of phthalocyanines incorporated into liquid crystal materials and their subsequent use in electro-optical devices.

The properties of spin coated films of compounds of the present invention are discussed hereinafter. Such spin coated films may be useful in the production of optical recording media, and also in sensors.

Sensors

Films of Pcs of the prior art have been used for as the active component in conductometric and optical based sensors. They may also have utility as selective gas sensors (e.g. for $N_2$), as demonstrated by the alteration in spectral properties which occurs in the presence of particular gasses e.g. HCl (see Figures below).

Langmuir-Blodgett (LB) Films

The materials of the current invention may also be incorporated in Langmuir-Blodgett (LB) films. LB films incorporating phthalocyanines of the current invention may be laid down by conventional and well known techniques, see R. H. Tredgold in 'Order in Thin Organic Films', Cambridge University Press, p74, 1994 and references therein. Generally an LB film is prepared by depositing a monolayer of a surface-active material onto a water surface; this may be done using well established techniques. The molecules of the surface active material align in the monolayer, the hydrophilic ends remaining in the water, and the hydrophobic end projecting out of the surface. By other known techniques this monolayer may be transferred essentially intact onto the surface of a solid substrate and further monolayers deposited on the layer on the substrate to form a film, i.e. an LB film.

LB films including compounds of the current invention may be used as optical or thermally addressable storage media.

Molecular Wires

The compounds of the current invention may also be used as molecular wires, see R. J. M. Nolte et al, Angew, Chem. Int. Ed. Eng., vol. 33, part 21, page 2173, 1994.

Photonic Devices

It is known that some phthalocyanines are excellent generators of third order non-linear optical effects and thus show promise for use in photonic devices including all-optical switches and computers, see Bredas, Adant, Tackx Persoons and Pierce, Chem. Rev., 94, p243, 1994. The materials of the present invention may show such effects and be used in such devices. In particular the distortion of the delocalised B system of the AzaPc which may be induced by the pyridine ring may be expected to produce novel properties as compared with prior art PCs used for this purpose.

Redox Applications

The compounds of the present invention allow for electronic interaction of substituents with the Azaphthalocyanine ring. The redox properties of the Azaphthalocyanines described by the current invention may be easily modified by the altering the identity of the various substituents. The compounds described by the current invention are therefore useful in any one or more of the following: electrocatalysis, photocatalysis, photovoltaics (e.g. solar cells), electric conduction, photoconductivity and electrochromism and other applications which exploit redox properties.

Polyelectrolytes

Polyethylene oxides can complex alkali metal ions, for example Li+ and have been used as polyelectrolytes in solid state battery applications, see Charadame in 'Macromolecules', ed. Benoit and Rempp, Pergamon press, New York, 1982, p226. The compounds of the invention may also be useful as polyelectrolytes, they are able to stabilise charge, therefore there exist a number of applications within battery technology.

Further aspects of the invention:

As well as use in the methods described above, in a further aspect of the invention there is a disclosed a method of preparing the compounds of the present invention, substantially as described hereinafter.

Dimers or higher oligomers comprising or consisting of the compounds of the present invention are also embraced within its scope. Particularly embraced are "edge-to-face" dimers, including mixed dimers formed between one compound of the present invention and another Pc or AzaPc.

It may be advantageous to polymerise certain of the compounds described by the current invention. Polymerised phthalocyanines may be used in, for example, LB films. There are numerous ways by which the phthalocyanine compound may be polymerised. Polymerisation may be effected via one or more of the positions $R_n$ or $R_p$ as described in formula I of the current invention or via the central metal atom or metal compound, or polymerisation may be realised by a combination of the above methods. An example of a suitable phthalocyanine substituent which may be used to effect polymerisation is an unsaturated substituent such as an alkene group.

Main chain or side chain liquid crystal polymers may also be made using the compounds of the present invention, or metal-linked liquid crystal polymers.

FIGURES

Figure 1A:
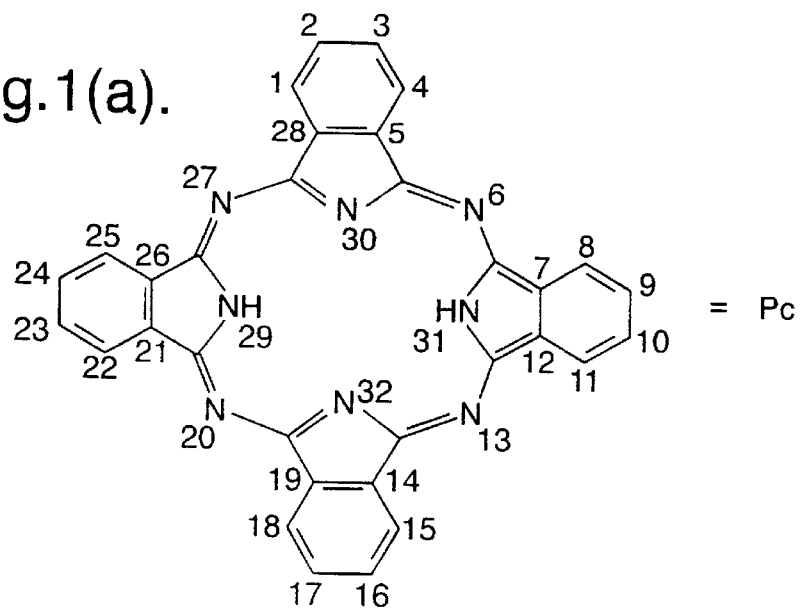
FIG. 1(a) shows Pc
Figure 1B:
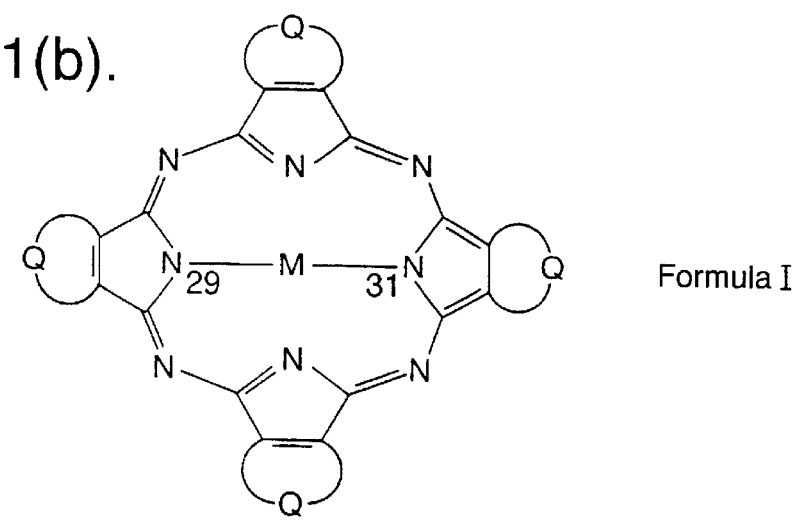
FIG. 1(b) shows Formula I
Figure 1C:
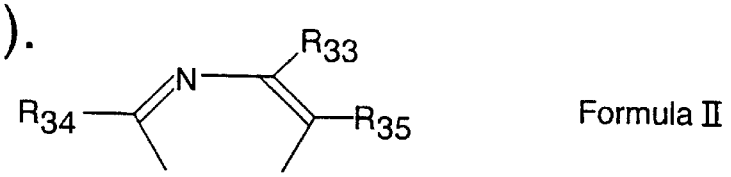
FIG. 1(c) shows Formula II
Figure 1D:
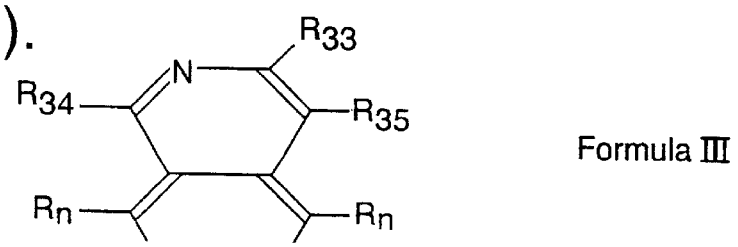
FIG. 1(d) shows Formula III
Figure 1E:
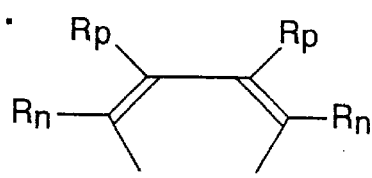
FIG. 1(e) shows Formula IV
Figure 1F:
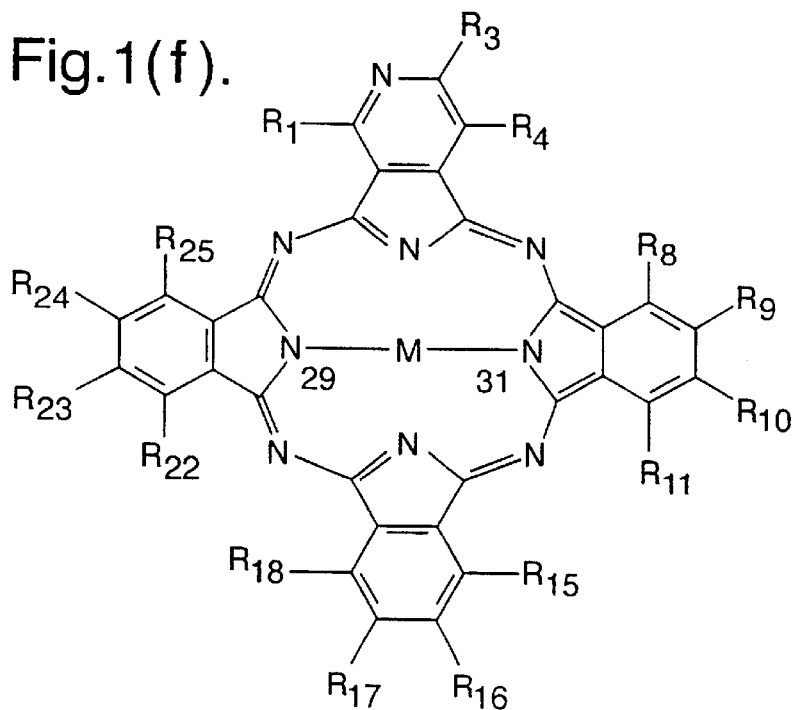
FIG. 1(f) shows Formula V
Figure 1G:
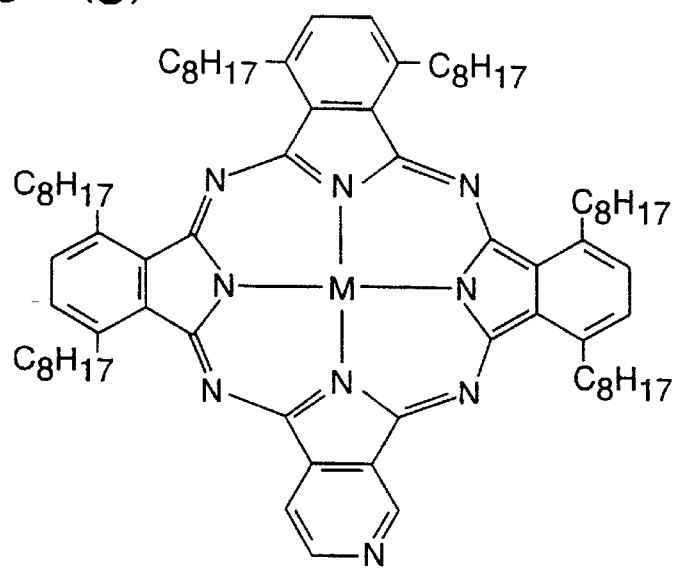
FIG. 1(g) shows Formula VI
Figure 1H:
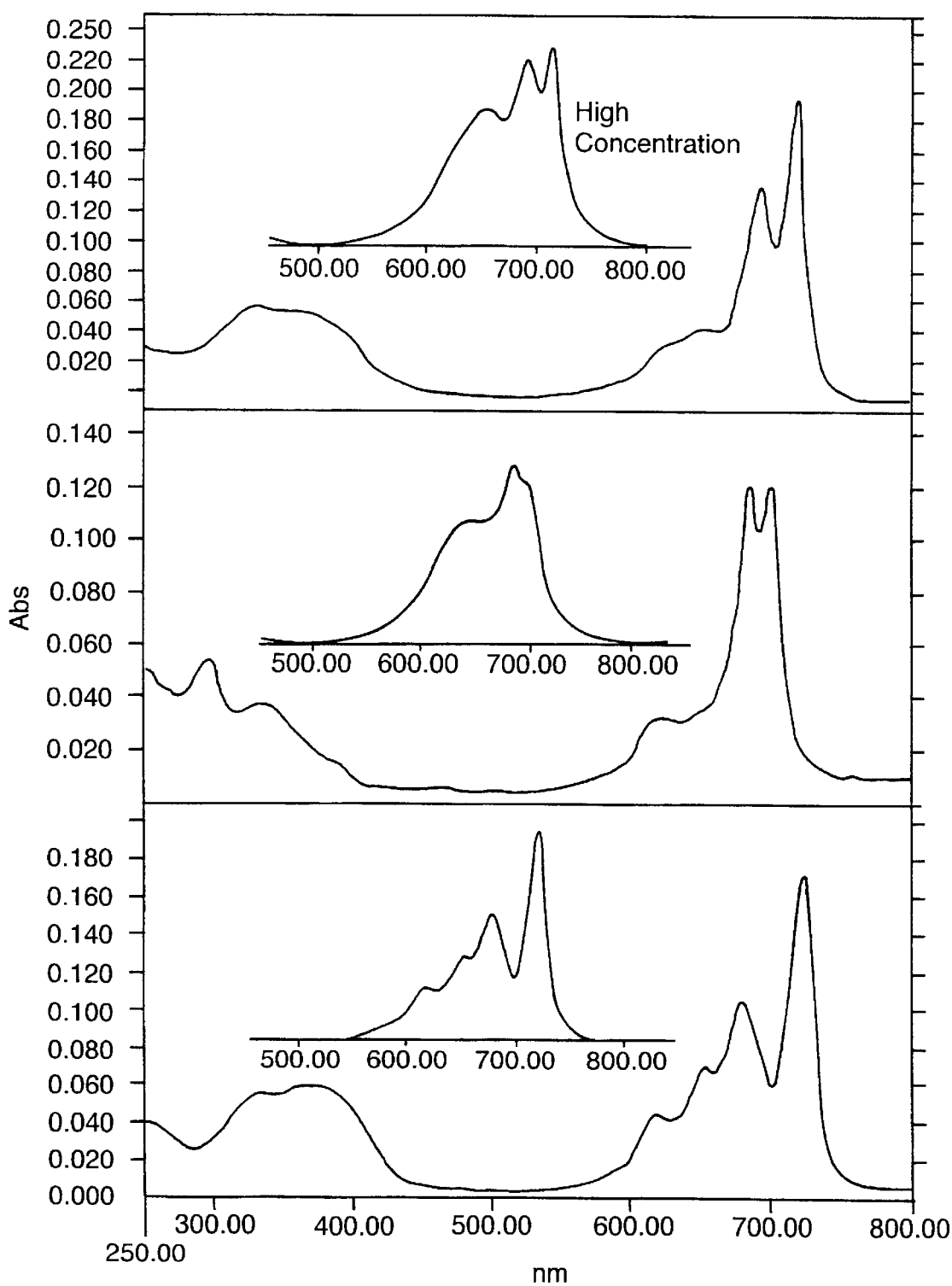
FIG. 1(h) shows.

Top. 250–800 nm spectrum of 1a as a solution in cyclohexane at $1.46 \times 10^{-6}$M; $\lambda_{max}$ 710 nm ($\epsilon 1.36 \times 10^5$), 687 nm ($\epsilon 0.95 \times 10^5$). Inset spectrum (scale not shown) shows the Q-band absorption at $1.46 \times 10^{-4}$M; $\lambda_{max}$ 709 nm ($\epsilon 6.23 \times 10^4$), 687 nm ($\epsilon 5.85 \times 10^4$), 652 nm ($\epsilon 4.33 \times 10^4$).

Middle, as above but for 1b at $1.04 \times 10^{-6}$M; $\lambda_{max}$ 694 nm ($\epsilon 1.16 \times 10^5$), 679 nm ($\epsilon 1.17 \times 10^5$). Inset spectrum, Q-band absorption at $1.04 \times 10^{-4}$M; $\lambda_{max}$ 690 nm ($\epsilon 5.61 \times 10^4$), 679 nm ($\epsilon 6.15 \times 10^4$), 643 nm (68 $4.27 \times 10^4$).

Bottom, as above but for 1c at $1.24 \times 10^{-6}$M; $\lambda_{max}$ 716 nm ($\epsilon 0.86 \times 10^5$). Inset spectrum, Q-band absorption at $1.24 \times 10^{-4}$M; $\lambda_{max}$ 715 nm ($1.25 \times 10^5$), 679 mn ($\epsilon 0.75 \times 10^5$).

FIG. 2

Transmission electron micrograph of 1b as a THF gel on a carbon coated copper grid. The field of view is 453×294 nm.

FIG. 3

Figure 3A:
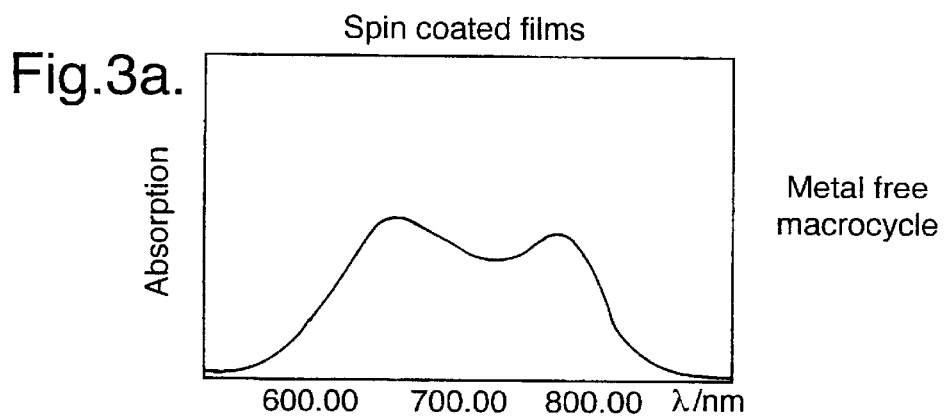
Figure 3B:
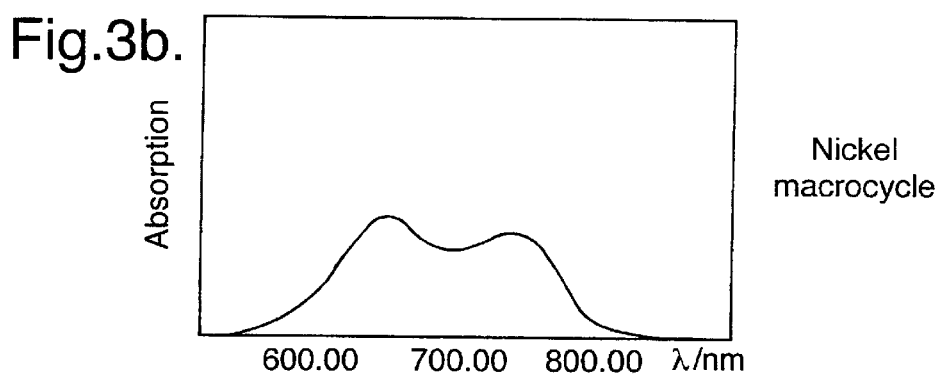
Figure 3C:
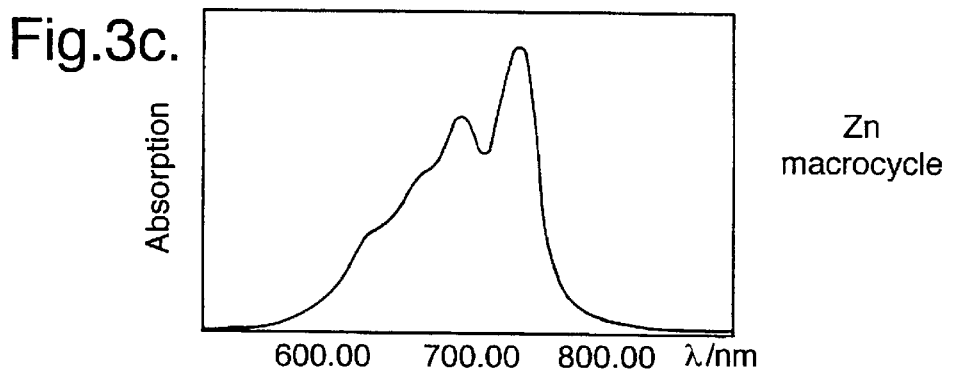
Figure 3D:
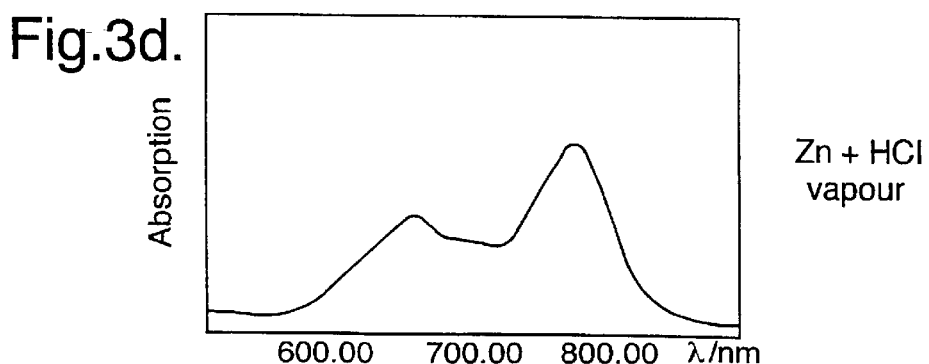

The visible region spectra of spin coated films of 1a (FIG. 3a), 1b (FIG. 3b) and 1c (FIG. 3c). FIG. 3d shows the film of 1c after exposure of Hcl vapour. Within 30 days after exposure to HCl, the film gives a spectrum the same as that in FIG. 3c.

FIG. 4

A liquid crystal device as described in Example 4.

FIG. 5

Some of the compounds of the present invention which were produced as described in Example 1.

FIG. 6

A putative mixed ("edge to face") dimer complex of the present invention.

FIG. 7

Scheme 1, showing phase transitions determined by DSC and optical microscopy. Enthalpy data were determined by DSC at a heating/cooling rate of 10° C. min$^{-1}$ K and $K_1$ refer to crystal phases. The higher temperature mesophase for 1a and 1b appears as a fan texture when viewed through a polarised light microscope, characteristic of a columnar mesophase with hexagonal cross sectional symmetry in which the columns are disordered; ie $D_2$. The lower temperature mesophase shows a needle type texture comparable with that assigned elsewhere to a second $D_1$ mesophase within the octaalkylphthalocyanine series.

EXAMPLES

Example 1

Preparation of Compounds of the Present Invention

Briefly, the novel macrocyclic derivative Formula VI, wherein M was 2H (designated 1a) was obtained by reaction of 3,4-dicyanopyridine with excess 3,6-dioctylphthalonitrile[9] under basic (lithium pentyloxide) conditions. Following conventional workup, 1a (10%) was separated chromatographically from the principal by-product, 1,4,8,11,15,18,22,25-octaoctylphthalocyanine.[9]

Figure 5:
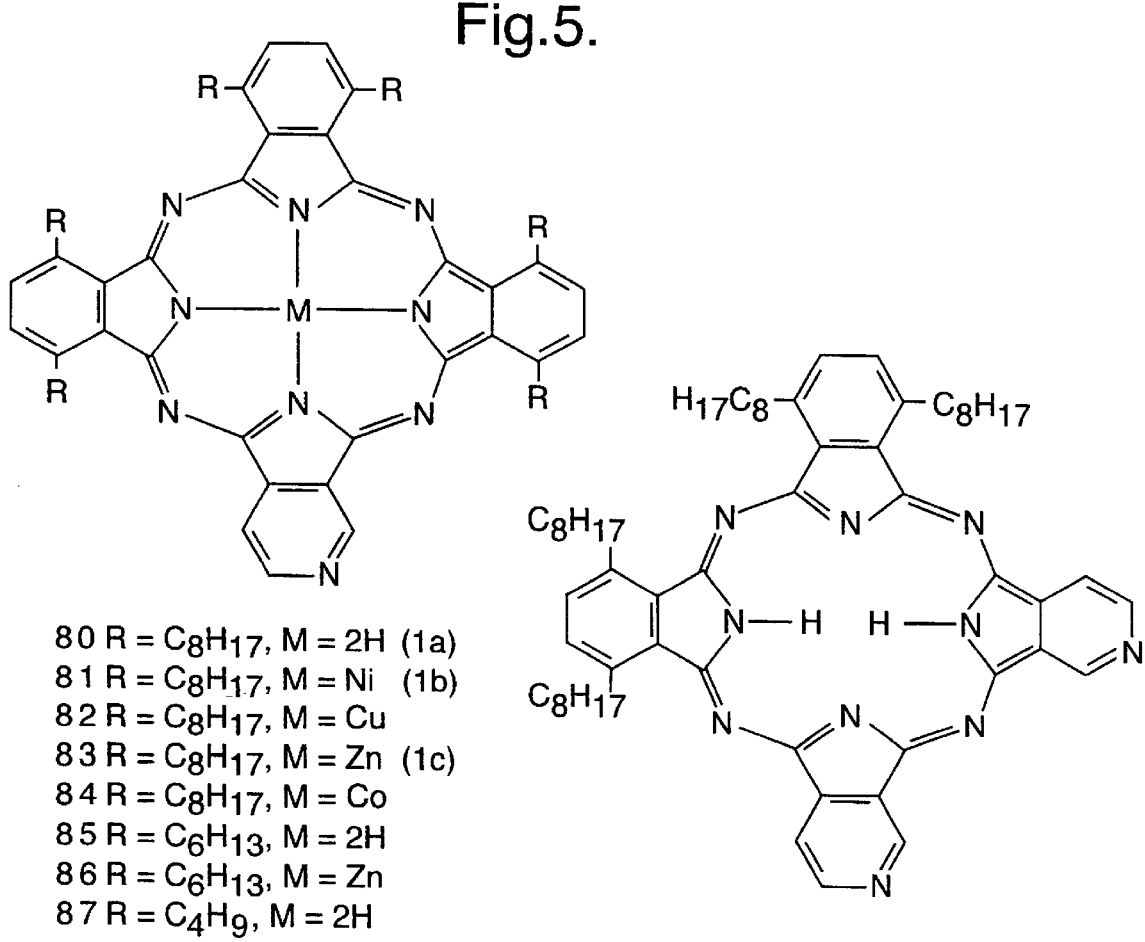

The compounds 81 to 88 shown in FIG. 5 were generated from the metal-free compound 80 (=1a) as exemplified by the Cu, Zn and Ni derivatives described below.

Preparation of 1,4,8,11,15,18-(hexaoctyl)tribenzo-3,4-pyridinoporphyrazine

In a typical procedure, 3,6-dioctylphthalonitrile (3.17 g, 9 mmol) and 3,4-dicyanopyridine (0.13 g, 1 mmol) in dry pentan-1-ol (30 ml) were heated under reflux with stirring and lithium metal (0.2 g) was added slowly in small portions. The solution turned an intense green colour immediately and reflux was continued for 6 hours, then the mixture was allowed to cool to room temperature and glacial acetic acid (50 ml) was added and stirring continued for 30 minutes. The solvents were removed under reduced pressure and the mixture washed onto a filter with methanol (500 ml) to remove non-phthalocyanine impurities, the rest of which were left on the filter when the Pcs were taken up in THF. The solvent was removed under reduced pressure and the mixture was separated using column chromatography over silica gel. The first green fraction contained only metal-free 1,4,8,11,15,18,22,25-octaoctylphthalocyanine using as eluent light petroleum. The next green fraction was collected, eluent THF, and further purified by column chromatography over silica gel, eluent cyclohexane-THF (9:1) and recrystallised from THF-methanol to afford 1,4,8,11,15,18-(hexaoctyl)tribenzo-3,4-pyridinoporphyrazine as a blue solid (125 mg, 10% based on 3,4-dicyanopyridine). Mp 142° C. (K-D), 242EC (D-I); FAB-MS (LSIMS) m/z 1188. (Found: C, 79.54; H, 9.55; n, 10.65. $C_{79}H_{113}N_9$ requires: C, 79.82; H, 9.58; n 10.60). $\nu_{max}$ (DCM)/cm$^{-1}$: 3285 (NH) and 1600 (aromatic); $\delta_H$ (270 MHZ; $C_6D_6$): -2.17 (br s, 2H), 0.85-0.96 (m, 18H), 1.20-1.95 (m, 60H), 2.2-2.5 (m, 12H), 4.10 (br s, 4H), 4.43 (M 4H), 4.54 (m, 4H), 7.65-7.8 (m, 4H), 7.86 (s, 2H), 8.53 (d, 1H), 9.14 (d, 1H), 10.35 (s, 1H); $\lambda_{max}$ (cyclohexane)/nm: 328, 687 and 710. The third fraction to be collected was obtained using cyclohexane-THF (2:1) as eluent and recrystallised from THF-methanol to afford di-3,4-pyridino-1,4,8,11-(tetraoctyl)dibenzo-porphyrazine as a dark blue solid (5 mg, 1% based on 3,4-dicyanopyradine). Mp 250EC (K-D), 326 (D-I); FAB (LSIMS) m/z 966; (Found: C, 77.25; H, 8.53; N, 14.24 $C_{62}H_{80}N_{10}$ requires: C, 77.14; H, 8.35; N,14.51). $\delta_H$ (270 MHZ; $C_6D_6$; 50EC): -4.35--3.83 (t, 2H), 0.95 (t, 12H), 2.15-2.41 (m, 8H), 3.94 (m, 4H), 4.20 (m, 4H), 7.59-7.74 (m, 4H), 8.19-8.30 (m, 2H), 8.96-9.03 (m, 2H), 10.04-10.15 (t, 2H). $\delta_{max}$ (cyclohexane)/nm: 324, 669, 705.

Preparation of Copper 1,4,8,11,15,18-(hexaoctyl)tribenzo-3,4-pyridinoporphyrazine In a typical procedure, copper(II) acetate (0.2 g) was added to a stirred solution of 1,4,8,11,15,18-(hexahexyl)tribenzo-3,4-pyridinoporphyrazine (70 mg) in pentan-1-ol (20 ml) and heated under reflux for 90 minutes. The solvent was removed under reduced pressure and the residue purified using column chromatography over silica gel using as eluent cyclohexane-THF (5:1) and recrystallised from THF-methanol to afford copper 1,4,8,11,15,18-(hexaoctyl)tribenzo-3,4-pyridinoporphyrazine as a blue solid (48 mg, 65%). Mp 134° C. (K-D), 319° C. (D-I); FAB (LSIMS) m/z 1249; (Found: C, 75.84: H, 9.00; N, 9.90. $C_{79}H_{111}N_9Cu$ requires: C, 75.89; H, 8.95; N, 10.08). $\lambda_{max}$ (cyclohexane)/nm: 325, 343 629, 649, 686, 701.

Preparation of Nickel and Zinc Derivatives

The Ni derivative (designated 1b) or Zn derivative (designated 1c) were produced by reactions of 1a with nickel acetate and zinc acetate in refluxing pentanol generated 1b (53%) and 1c (78%). Each gave a satisfactory elemental analysis and low resolution FAB-ms as follows: Found: C, 79.54; H, 9.55, N, 10.65; $C_{79}H_{113}N_9$ requires: C, 79.82; H, 9.58; N, 10.60. 1b, Found: C, 76.10; H, 9.00; N, 9.95; $C_{79}H_{111}N_9Ni$ requires: C, 76.18; H, 8.98; N, 10.12. 1c, Found: C, 75.68; H, 8.78; N, 9.95; $C_{79}H_{111}N_9Zn$ requires: C, 75.78; H, 8.94; N, 10.07.

All three compounds (1a, 1b, 1c) showed good solubility in solvents such as THF, toluene, cyclohexane and dichloromethane.

Compounds of the present invention based on a napthalocyanine structure (i.e. azanapthalocyanines) can be prepared by methods analogous to those described above, in conjunction with the disclosure of Cammidge et al (1997) J Porphyrins Pthalocyanines 1:77–86.

Example 2

Spectra of the Compounds

The properties of the substituted pyridino[3,4]-tribenzoporphyrazines, 1, prove to be highly dependent upon the atom(s) at the centre of the macrocycle and reflect the individual compound's propensity for forming either Face-to-Face assemblies or Edge-to-Edge complexes. The Q-band absorptions in the visible region spectra of solutions of 1a (2H) and 1b (Ni) in cyclohexane at ca. $1 \times 10^{-6}$M are shown in FIG. 1. The two component Q-band of 1a, top spectrum in FIG. 1, is similar to that of a metal-free Pc. The Q-band of 1b, the middle spectrum, is also split $\lambda_{mas}$ 694 and 679 nm, differing from that of simple metallated Pcs but consistent with the lower symmetry of the system.[10] Otherwise, the high extinction coefficients of the Q-bands, see legend to FIG. 1, and the very low intensity absorptions to the blue are characteristic of Pc compounds which are essentially non aggregated. At high concentrations, however, Face-to-Face type aggregation becomes apparent, manifested by the characteristic enhanced absorption in the region 600 to 690 nm (see the inset spectra in FIG. 1) and the lower extinction coefficients of the lowest energy bands.

The zinc derivative, 1c, shows different behaviour. The spectrum of 1c in cyclohexane, the bottom spectrum in FIG. 1, and in dichloromethane shows enhanced separation of the main Q-band components, $\lambda_{max}$ 716 and 675 nm, within a band envelope which is essentially invariant over the concentration range ca. $1 \times 10^{-7}$M. In particular, extinction coefficients remain high at the higher concentrations. Absence of Face-to-Face aggregation is signified by the lack of significant absorption in the visible region to the blue of these main bands. The gel permeation chromatogram obtained for elution of 1c as a solution in dichloromethane through PLgel 100A and 500A, 30 cm, 5 micron columns and calibrated against polystyrene gives a peak molecular mass, Mp, of 2050 ($M_w$ 1630 and $M_n$ 1390). Elution of three model phthalocyanine derivatives under the same conditions showed that the "polystyrene equivalent" molecular masses for these macrocycles are consistently 20–25% lower than the actual molecular mass. Thus the Mp obtained for 1c suggests that under the conditions of the GPC experiment, the material has formed a dimeric complex.

Thus we assign the visible region spectrum of 1c, above, to a dimeric species (or lower oligomeric species) arising from intermolecular axial ligation of a pyridyl nitrogen of one macrocycle with the zinc atom of a second, to form an Edge-to-Face complex. In support of this, we note that addition of pyridine or THF changes the band shape to one closely resembling that of non-aggregated 1b; this we attribute to disruption of the homoligated complex of 1c. Similarly, excitation of 1c ($\lambda_{ex}$ 650 nm) as a solution in toluene at 1.2–10$^{-5}$M shows fluorescence emission at $\lambda_{max}$ 731 nm. Addition of 100 Fl pyridine raises the emission intensity by a factor of two and shifts the emission band to 720 nm. In contrast 1a under the same conditions shows $\lambda_{em\_}$721 nm, essentially unchanged when pyridine is added.

Further confirmation of the formation of Edge-to-Face complexes by 1c was obtained by $^1$H-NMR spectroscopy. The spectrum of 1c in benzene-d$_6$ shows no signals downfield of $\delta$8.32. Upon addition of pyridine-d$_5$, the spectrum simplifies and is very similar to that of 1a. In particular, the pyridyl protons of 1c now appear at 9.25, 9.43 and 11.12 ppm. We believe it likely that higher oligomers may be present at the higher solution concentrations used in the NMR experiment. NMR spectroscopy of 1a (Ni derivative) at 1 mM suggests some degree of edge-to-face structure, in addition to UV-VIS evidence suggesting face-to-face structures which is discussed above.

Example 3

TEM

Figure 2:
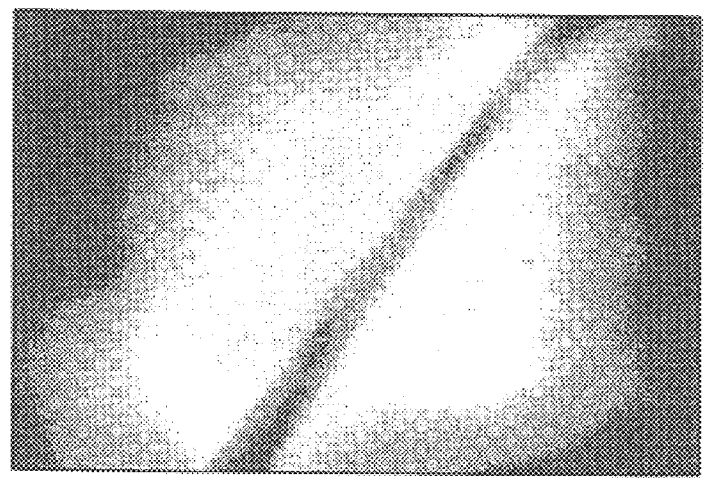

Transmission electron microscopy highlighted differences in packing in the condensed states of 1a, 1b, and 1c. A drop of a solution of each compound in THF (2 mg per ml) was administered onto a copper grid, blotted dry, and viewed through a JEOL 100CX Electron Microscope as the solvent evaporated. FIG. 2 shows the micrograph obtained for 1b. It clearly shows the generation of a columnar structure, formally analogous to the "molecular wires" observed by Nolte et al.[11] for a more complex Pc derivative. Compound 1a showed similar behaviour. The width of the assembly depicted in FIG. 2 is ca. 15 times the approximate diameter of the individual molecules of 1b. In contrast, 1c forms a distinctly different structure, the micrograph showing an apparently featureless film with no evidence of column formation.

Example 4

LC Properties

Figure 7:
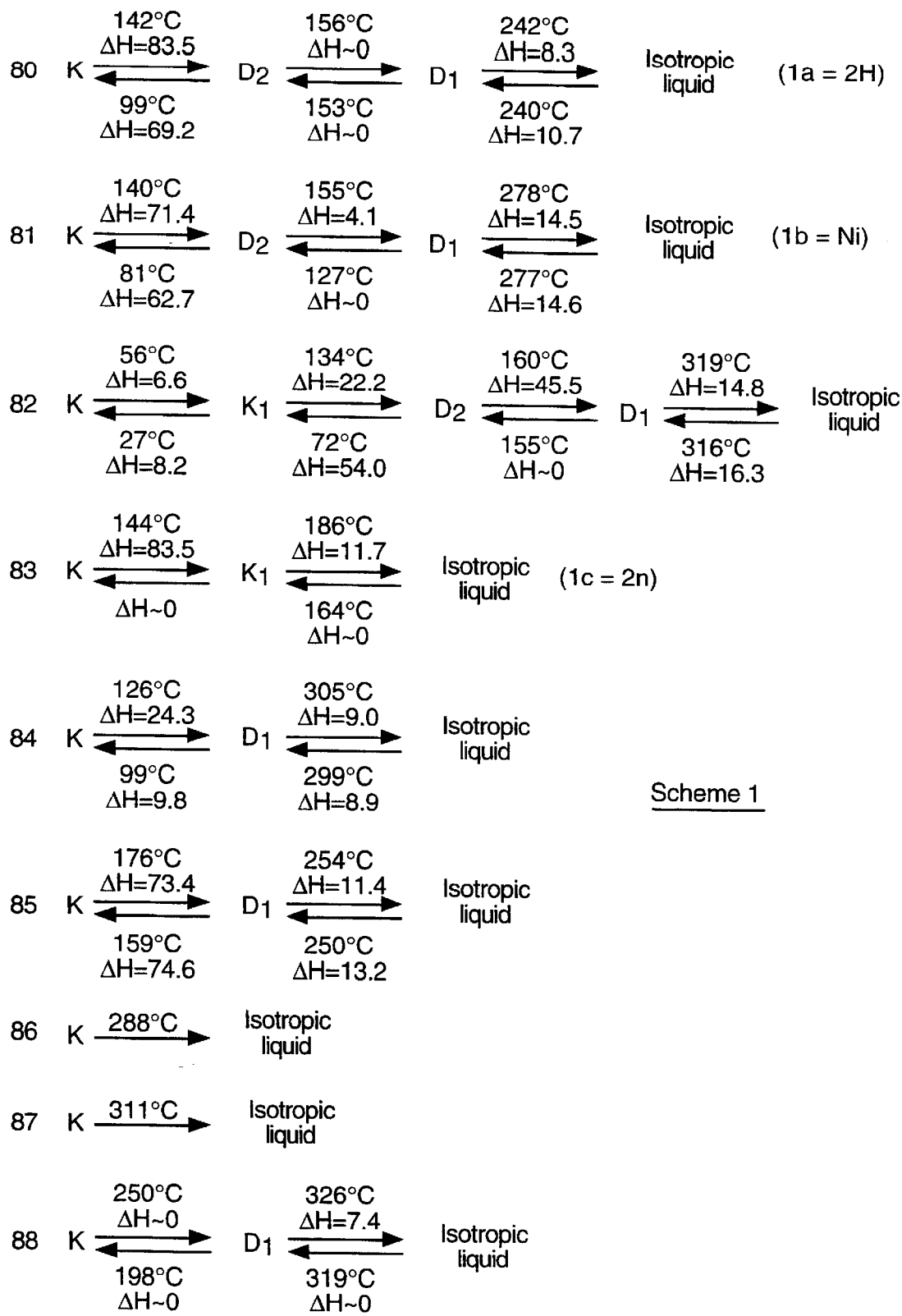

The differences in the molecular packings in the condensed phase lead to different behaviour on heating and cooling. Thus, compounds 1a and 1b exhibit thermotropic columnar mesophases; polarised light microscope shows a fan type structure on cooling from the isotropic liquid consistent with the hexagonal columnar mesophase exhibited by other non-peripherally alkyl-substituted Pcs.[12] Phase transition data are reported in Scheme 1 (FIG. 7). In contrast, 1c does not exhibit a mesophase during either heating of the solid sample or upon cooling from the liquid phase; this we attribute to the orthogonal packing of adjacent molecules in the solid state and, presumably, in the liquid state just prior to crystallisation.

Example 5

Spin Coated Films

Large area evaporated films were formulated by the spin coating technique by administering a drop of solution of each compound in THF (ca. 2 mg in 0.5 ml) onto a glass slide rotating a 2000 rpm. Films so formed were transparent and showed no crystallites when viewed under an optical microscope. Their visible region spectra are shown in FIG. 3a–3c. Those for the films of 1a and 1b are closely similar to the spectra of films of metal-free and nickel 1,4,8,11,15, 18,22,25-octa-octylphthalocyanines respectively[12] whereas the film spectrum for 1c, FIG. 3c, is similar to its solution phase spectrum, albeit blue-shifted by ca. 10 nm. Exposure of the latter film to pyridine vapour did not change the spectrum. However, the assembly became disrupted upon exposure to HCl vapour. The new spectrum is shown in FIG. 3d. Within 30 days the original spectrum was recovered, implying that the response to HCl is fully reversible and the molecules reassemble to give the intermolecular complex.

In conclusion, we have identified a phthalocyanine type macrocycle whose molecular packing is governed by the central metal ion. Both Face-to-Face and Edge-to-Face packing has been identified. The latter is promoted by the propensity for zinc to undergo strong axial ligation and columnar liquid crystal behaviour, otherwise inherent within the series, is inhibited. Nickel complexes may also undergo weak axial ligation. However, 1b at UV/vis concentrations and in the liquid crystal phases favours Face-to-Face structures in which the Ni(II) d$^8$ ion is presumably in its favoured spin paired, square-planar four coordinate state.

Example 6

An LCD Device

Figure 4:
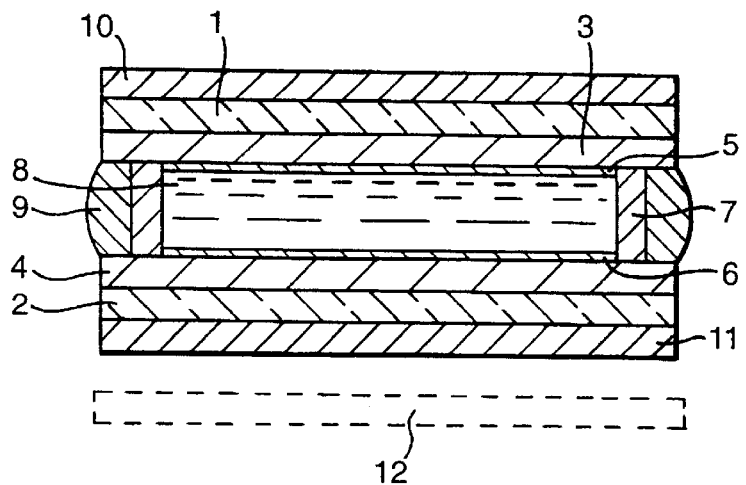

An example of the use of a compound of Formula I in a liquid crystal material and device embodying the present invention will now be described with reference to FIG. 4.

The liquid crystal device consists of two transparent plates, 1 and 2, in this case made from glass. These plates are coated on their internal face with transparent conducting electrodes 3 and 4. An alignment layer 5, 6 is introduced onto the internal faces of the cell so that a planar orientation of the molecules making up the liquid crystalline material will be approximately parallel or at a small angle to the glass plates 1 and 2. For some types of display the plane of the molecules is approximately perpendicular to that of the glass plates, and at each glass plate the alignment directions are orthogonal. The electrodes 3, 4 may be formed into row and column electrodes so that the intersections between each column and row form an x, y matrix of addressable elements or pixels. A spacer 7 e.g. of polymethyl methacrylate separates the glass plates 1 and 2 to a suitable distance e.g. 2 microns. Liquid crystal material 8 is introduced between glass plates 1, 2 by filling the space in between them. The spacer 7 is sealed with an adhesive 9 in a vacuum using an existing technique. Polarisers 10, 11 are arranged in front of and behind the cell. For some devices, only one or even no polarisers are required.

The device may operate in a transmissive or reflective mode. In the former, light passing through the device, e.g. from a tungsten bulb, is selectively transmitted or blocked to form the desired display. In the reflective mode a mirror (12) is placed behind the second polariser 11 to reflect ambient light back through the cell and two polarisers. By making the mirror partly reflecting the device may be operated both in a transmissive and reflective mode.

The alignment 5, 6 have two functions one to align contacting liquid crystal molecules in a preferred direction and the other to give a tilt to these molecules—a so called a surface tilt—of a few degrees typically around 4 or 5°. The alignment 5, 6 may be formed by placing a few drops of the polyimide onto the cell wall and spinning the wall until a uniform thickness is obtained. The polyimide is then cured by heating to a predetermined temperature for a predetermined time followed by unidirectional rubbing with a roller coated with a nylon cloth.

Example 7

Gas Sensor

In another example a layer of liquid crystal material is exposed to a gas to provide a gas sensor.

Example 8

Mixed Dimers

Figure 6:
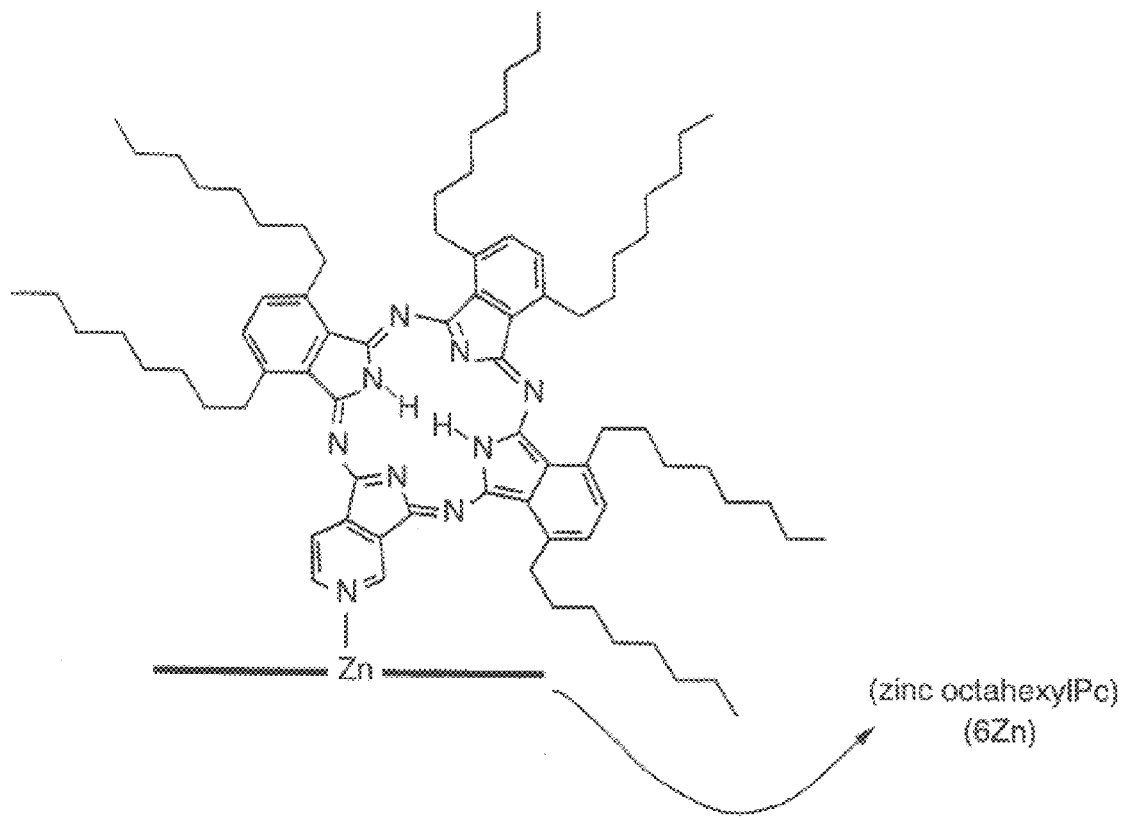

Upon introduction of 1.0 eq of Zn 1,4,8,11,15,18,22,25-octahexylphthalocyanine (designated 6Zn in FIG. 6) into the $^1$H NMR solution of compound 80 in $C_6D_6$ there was no signal observed downfield of $\delta 8.05$. Prior to this addition the signals for the pyridyl protons appeared 8.53, 9.14, 10.35 ppm. Instead of three signals representing the methylene protons next to the ring, four signals appear. This seems to suggest that on formation of a dimeric complex through the coordination of the pyridine unit of compound 80 to the zinc centre of the 6Zn; the ring current of the 6Zn shields two methylene protons of 80 to a significant degree causing an upfield shift of 0.43 ppm. The N-H proton of 80 is shifted downfield by 0.55 ppm.

REFERENCES

1. Phthalocyanines—Properties and Applications, eds. Leznoff and Lever, VCH Publishers, New York, 1989.
2. Cook, in Spectroscopy of New Materials, eds. Clark and Hester, Wiley, Chichester, 1993,p.87.
3. Simon and Bassoul, in Phthalocyanines—Properties and Applications, eds. Leznoff and Lever, VCH Publishers, New York, 1993, vol.2,p.223.
4. See, for example, Mason et al. J.Chem.Soc., Dalton Trans. 1979,676.
5. Pomogailo and Wöhrle, in Macromolecule-Metal Complexes, eds. Ciardelli et al. Springer, Berlin-Heidleberg, 1996, p.11; Hanack and Lang, Adv. Mater, 1994,6,819.
6. Eg. Shachter et al., J.C.S.Chem.Commun. 1988, 960; Fleischer and Shachter, Inorg.Chem., 1991,30, 3763;Hunter and Sarson, J.C.S.Chem.Commun., 1994,33, 2313; Funatsu et al., Chem.,Lett., 1995,765; Anderson et al., Angew.Chem.Int.Ed.Engl., 1995,34,1096; Alessio et al., J.C.S.Chem.Commun., 1996,1411–1412.
7. Linstead et al., J.Chem.Soc., 1937,911.
8. Yokote and Shibamiya. Kogyo Kagaku Zasshi, 1959,62, 224. Chem.Abs. 1961,24019; Yokote el al., Kogyo Kagaku Zasshi, 1964, 67, 166. Chem.Abs. 61, 3235; Yokote et al.. Yuki-Gosei Kagaka Kyokaishi 1965,23,151. Chem.Abs. 71,38931h; Sakamoto and Shibamiya, J.Japn.Soc.Colour Material, 1985,58,121; Sakamoto and Shibamiya, J.Japn.Soc.Colour Material, 1986,59,517.
9. Chambrier et al., J.Mater.Chem., 1993,3,841.
10. cf. Kobayashi et al., J.Am.Chem.Soc., 1996,118,1073; Cook and Jafari-Fini, J.Mater.Chem., 1997,7,5.
11. van Nostrum et al., Angew.Chem., Int.Ed.Engl., 1994, 33,2173; van Nostrum et al., J.Am.Chem.Soc., 1995,117, 9957.
12. Cherodian et al., Mol.Cryst.Liq.Cryst., 1991,196,103.

What is claimed is:

1. A compound having formula V;

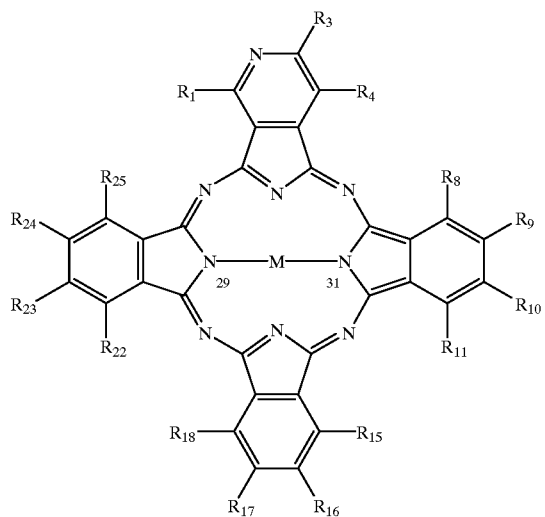

Formula V wherein

M is selected from:
  a metal atom; a metal compound; 2H whereby one H is bonded to each of the two nitrogen atoms depicted as being bonded to M (positions 29 and 31 shown)

$R_1$, $R_3$, $R_4$, $R_9$, $R_{10}$, $R_{16}$, $R_{17}$, $R_{23}$, and $R_{24}$ are H;

$R_8$, $R_{11}$, $R_{15}$, $R_{18}$, $R_{22}$, and $R_{25}$ are the same or different and are independently selected from:
  $C_1$ to $C_{32}$ alkyl; $C_2$ to $C_{32}$ alkenyl; X—O—Y; X—phenyl, $X^2COOX^1$, $X^2CONR^1R^{11}$, H; halide;

wherein:

X and $X^2$ are independently selected from: a chemical bond, —$(CH_2)_n$—wherein n is an integer from 1 to 32, —$(CH_2)_a$—CH=CH$(CH_2)_b$ where a and b are independently selected from integers 0–32 and a+b totals 32;

$X^1$ and Y are independently selected from: $C_1$ to $C_{32}$ alkyl, $C_2$ to $C_{32}$ alkenyl, and H;

$R^1$ and $R^{11}$ are independently selected from: H; $C_1$ to $C_{32}$ alkyl, and $C_2$ to $C_{32}$ alkenyl, with the proviso that at least one of $R_8$, $R_{11}$, $R_{15}$, $R_{18}$, $R_{22}$, and $R_{25}$ is selected from: $C_1$ to $C_{32}$ alkyl, $C_2$ to $C_{32}$ alkenyl, X—O—Y, X—phenyl, $X^2COOX^1$, $X^2CONR^1R^{11}$.

2. A compound as claimed in claim 1 wherein all non-peripheral R groups other than those attached to pyridyl nuclei are selected from: alkyl containing up to 32; up to 20; between 4–14; or between 8–12 C atoms where one or more adjacent $CH_2$ groups may be replaced by O or a double bond, and the remaining R groups are all H.

3. A compound as claimed in claim 1 wherein alkyl groups present within the R groups are straight chain alkyl.

4. A compound as claimed in claim 1 wherein M is selected from: 2H; Ru, Ni, Pb, V, Pd, Co, Nb, Al, Sn, Zn, Cu, Mg, Ca, In, Ga, Fe, Eu, Lu and Ge.

5. A compound as claimed in claim 4 wherein M is selected from: 2H; Zn; Cu; Co; Ru; and Ni.

6. A compound as claimed in claim 5 having formula VI

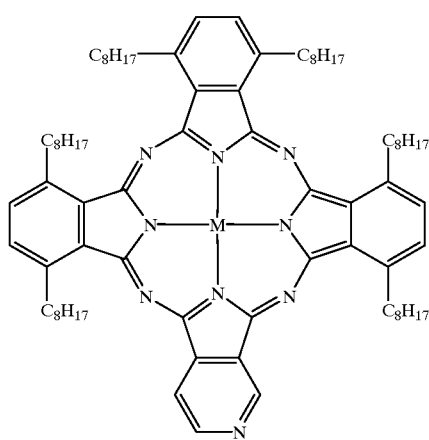

Formula VI wherein M in selected from: 2H; Zn; Ni.

7. A compound as claimed in claim 1 which has an absorption maximum in the near infra-red.

8. A composition comprising a compound as claimed in claim 1 in a carrier.

9. A pharmaceutical composition comprising a compound of claim 1 in admixture with a pharmaceutically acceptable carrier.

10. A pharmaceutical composition as claimed in claim 9 which is in the form of solution suitable for injection into a patient.

11. A dimer consisting of a compound as claimed in claim 1.

* * * * *